(12) United States Patent
Hosaka et al.

(10) Patent No.: US 11,905,499 B2
(45) Date of Patent: Feb. 20, 2024

(54) HIGH-PURITY ISOPROPYL ALCOHOL AND METHOD FOR MANUFACTURING SAME

(71) Applicant: TOKUYAMA CORPORATION, Yamaguchi (JP)

(72) Inventors: Shunsuke Hosaka, Yamaguchi (JP); Masanari Ishizuki, Yamaguchi (JP)

(73) Assignee: TOKUYAMA CORPORATION, Yamaguchi (JP)

( * ) Notice: Subject to any disclaimer, the term of this patent is extended or adjusted under 35 U.S.C. 154(b) by 249 days.

(21) Appl. No.: 17/281,712

(22) PCT Filed: Sep. 30, 2019

(86) PCT No.: PCT/JP2019/038491
§ 371 (c)(1),
(2) Date: Mar. 31, 2021

(87) PCT Pub. No.: WO2020/071307
PCT Pub. Date: Apr. 9, 2020

(65) Prior Publication Data
US 2022/0002641 A1 Jan. 6, 2022

(30) Foreign Application Priority Data
Oct. 3, 2018 (JP) ................................ 2018-188017

(51) Int. Cl.
*C11D 7/50* (2006.01)
*C11D 7/26* (2006.01)
*C07C 29/80* (2006.01)
*C11D 11/00* (2006.01)

(52) U.S. Cl.
CPC ............. *C11D 7/261* (2013.01); *C07C 29/80* (2013.01); *C11D 7/5022* (2013.01); *C11D 11/0047* (2013.01)

(58) Field of Classification Search
CPC .................................................. C07C 29/04
USPC ......................................... 510/175; 568/895
See application file for complete search history.

(56) References Cited

U.S. PATENT DOCUMENTS

| | | | |
|---|---|---|---|
| 5,868,906 | A | 2/1999 | Adams et al. |
| 6,733,637 | B1 | 5/2004 | Burton et al. |
| 9,120,724 | B2 † | 9/2015 | Sasaki |
| 2004/0158108 | A1 | 8/2004 | Snoble et al. |

FOREIGN PATENT DOCUMENTS

| | | |
|---|---|---|
| CN | 102755759 A | 10/2012 |
| CN | 112999679 A | 6/2021 |
| JP | H11506431 A | 6/1999 |
| JP | 2002121160 A | 4/2002 |
| JP | 3414595 B2 | 6/2003 |
| JP | 2003-535836 A | 12/2003 |
| JP | 2010-159212 A † | 7/2010 |
| JP | 2016004902 A | 1/2016 |
| JP | 2016179956 A | 10/2016 |
| JP | WO/2017/217279 A1 † | 12/2017 |
| KR | 10-2004-0085710 A † | 10/2004 |
| TW | 408104 B | 10/2000 |
| WO | 1996036412 A1 | 11/1996 |
| WO | 2001/094284 A2 | 12/2001 |
| WO | 2017217279 A1 | 12/2017 |
| WO | 2018/135408 A1 | 7/2018 |

OTHER PUBLICATIONS

Rong, Q. et al. "Theory and Application of Glow Discharge Mass Spectrometry" Shanghai Science and Technology Press. 2017. pp. 71. (2 pages).
Office Action issued in corresponding Chinese Application No. 201980062444.9, dated Sep. 28, 2021, with English translation (6 pages).
"The fifth series of experimental chemistry—Fundamental Techniques for Chemical Experiments—", 5th edition, Maruzen Co., Ltd., 2005, pp. 73-74 (3 pages).
"Chemistry dictionary 1", Kyoritsu Shuppan Co., Ltd., Mar. 30, 1960, pp. 638 (2 pages).
"12996 Chemical Products", The Chemical Daily Co., Ltd., Jan. 24, 1996, pp. 366-367 (3 pages).
Notice of Reasons for Rejection issued to JP Application No. 2020-545197, dated Oct. 27, 2020 (5 pages).
International Search Report issued in International Application No. PCT/JP2019/038491, dated Dec. 10, 2019 (2 pages).
Written Opinion issued in International Application No. PCT/JP2019/038491, dated Dec. 10, 2019 (4 pages).
Notice of Third Party Observations issued in related Taiwanese Application No. TW108135662, dated Sep. 11, 2023 (26 pages).
Prof. Steven Farmer, et al., 5) "12.9 Reactions of Aldehydes and Ketones with Alcohols," published Sep. 4, 2014 by LibreTexts Chemistry at https://chem.libretexts.org/Bookshelves/Organic_Chemistry/Map%3A_Essential_Organic_Chemistry_(Bruice)/12%3A_Carbonyl_Compounds_II%3A_Reactions_of_Aldehydes_and_Ketones_More_Reactions_of_Carboxylic_Acid_Derivatives/12.09%3A_Reactions_of_Aldehydes_and_Ketones_with_Alcohols.†

† cited by third party

*Primary Examiner* — Gregory E Webb
(74) *Attorney, Agent, or Firm* — Osha Bergman Watanabe & Burton LLP

(57) ABSTRACT

Provided is a high-purity isopropyl alcohol in which the concentration of a C7-12 acetal compound is 100 ppb or less on a mass basis, the concentration of the acetal compound in an accelerated test involving heating for 4 hours at 80° C. in a nitrogen atmosphere is increased by a factor of 30 or less with respect to the value thereof prior to heating, and the concentration of the acetal compound is maintained at a value of 100 ppb or less on a mass basis. Also provided is a method for manufacturing said high-purity isopropyl alcohol.

2 Claims, No Drawings

HIGH-PURITY ISOPROPYL ALCOHOL AND METHOD FOR MANUFACTURING SAME

TECHNICAL FIELD

The present invention relates to a high-purity isopropyl alcohol and a method for manufacturing the same.

BACKGROUND ART

Isopropyl alcohol (also referred to as 2-propanol) is an organic solvent which is used in various applications, and is manufactured by, for example, a hydration method of hydrating propylene.

Isopropyl alcohol is normally manufactured in a petrochemical complex capable of supplying propylene serving as a raw material, is transported to a demand area after being manufactured and is stored in a storage tank. As described above, isopropyl alcohol is often stored for a long time after being manufactured until use. Hence, it is a serious problem that the amount of impurity in isopropyl alcohol is increased when isopropyl alcohol is stored for a long time.

In particular, when isopropyl alcohol in which the amount of impurity is increased due to long-term storage is used for the cleaning application of an electronic device such as a semiconductor device, a residue derived from the impurity in the isopropyl alcohol may be left on the surface of the electronic device after cleaning and drying.

For example, Patent Document 1 discloses that an organic impurity dissolved in isopropyl alcohol is aggregated by the evaporation of the isopropyl alcohol so as to form a relatively large particle, and that the particle is left in a material to be treated so as to cause particulate pollution (particulate defect).

Since as described above, a residue after cleaning and drying becomes a factor in causing a defect in an electronic device, it is desired to minimize as much as possible the concentration of an organic impurity in isopropyl alcohol used as a cleaning liquid; in particular, the concentration of an organic impurity which is a residue after treatment and whose boiling point is higher than that of isopropyl alcohol. It is also desired to provide an isopropyl alcohol in which even when the isopropyl alcohol is stored for a long time, the amount of organic impurity causing a residue after cleaning and drying is not increased.

With respect to an increase in the amount of impurity during the storage of isopropyl alcohol, for example, Patent Document 2 discloses that an electron donor for a peroxy radical generated by the oxidation reaction of isopropyl alcohol is made to exist in the isopropyl alcohol so as to be able to highly suppress the progress of oxidative deterioration, and that thus it is possible to significantly reduce the amount of ketone generated during the storage of the isopropyl alcohol.

Patent Document 3 discloses that isopropyl alcohol is distilled and that thus an impurity whose boiling point is higher than that of isopropyl alcohol is removed. Patent Document 3 also discloses that, by combination with the removal of the high-boiling point impurity, an organic impurity whose boiling point is lower than that of isopropyl alcohol is distilled so as to be removed. Patent Document 3 suggests that these impurities in isopropyl alcohol are left on a wafer in a semiconductor manufacturing operation so as to cause a defect.

Patent Document 1: Japanese Unexamined Patent Application, Publication No. 2016-004902

Patent Document 2: Japanese Unexamined Patent Application, Publication No. 2016-179956

Patent Document 3: PCT International Publication No. WO01/094284

DISCLOSURE OF THE INVENTION

Problems to be Solved by the Invention

However, in Patent Document 3, the specific species of the high-boiling point impurity and the low-boiling point organic impurity are not clarified at all, and what types of these impurities act together and how they act together to cause a failure in the semiconductor application described above are not disclosed at all. Hence, the removal of an organic impurity is still on such a level as to obtain general quality for isopropyl alcohol, and thus the removal of an organic impurity is intended only for atmospheric distillation which is performed in a general industrial process. Consequently, the total amount of organic impurity is so large as to be 200 to 500 ppm (see paragraph [0018]).

The present inventors have conducted a study to find that there is an impurity in which an increase in its concentration cannot be suppressed only by making an electron donor for a peroxy radical exist in isopropyl alcohol. In particular, in recent years, it has been found that even when quality control at the time of manufacturing and shipment is performed such that a management value for an impurity whose boiling point is equal to or greater than 120° C. (required in isopropyl alcohol for the electronic industry), that is, a range in which its concentration is equal to or less than 50 ppb by mass, is satisfied, the concentration of an impurity derived from an organic substance may be increased during transportation and storage.

The present inventors have further conducted a study to find that in the impurity derived from the organic substance described above, an acetal compound generated by the condensation of an aldehyde compound and an alcohol compound exists, and that the amount of acetal compound described above is increased with time during storage.

An object of the present invention is to provide a high-purity isopropyl alcohol in which the concentration of an acetal compound that is an impurity is low, in which an increase with time in the concentration of the acetal compound is suppressed and which is excellent in long-term storage stability and a method for manufacturing such a high-purity isopropyl alcohol.

Means for Solving the Problems

The present inventors have conducted a thorough study in order to solve the problem described above. Consequently, the present inventors have found that it is possible to solve the problem described above not only by directly reducing the amount of acetal compound included as an impurity in isopropyl alcohol (composition) but also by controlling the concentration of an aldehyde compound having 1 to 6 carbon atoms such that the concentration is equal to or less than 1500 ppb by mass, and thereby have completed the present invention. The present inventors have also found that it is possible to more significantly reduce the concentration of the acetal compound by controlling the concentration of a ketone compound having 3 to 6 carbon atoms that the concentration is equal to or less than 2000 ppb by mass. It can be thought that the aldehyde compound having 1 to 6 carbon atoms or the aldehyde compound described above and the ketone compound having 3 to 6 carbon atoms are changed into an acetal compound due to some influence during storage. The amounts of these impurities are reduced, and thus it is possible to suppress an increase with time in the amount of acetal compound, with the result that an isopropyl alcohol in which the concentration of the acetal compound is maintained to be low is obtained.

Conventionally, it is thought that in an aldehyde compound and a ketone compound each having 1 to 6 carbon atoms, in particular, in an aldehyde compound and a ketone compound each having 1 to 3 carbon atoms, the boiling points thereof are often lower than that of isopropyl alcohol, and that thus even when they are used for the cleaning application of an electronic device, they are not left in a material to be treated. Hence, in reality, the contents thereof are not strictly controlled, and only the amounts thereof removed by atmospheric distillation performed in a general industrial process for removing a low-boiling point organic impurity are reduced.

Under these circumstances, the present inventors have succeeded in finding, for the first time, an isopropyl alcohol in which a high-boiling point organic impurity is significantly removed so as to make the concentration of the acetal compound equal to or less than 100 ppb by mass, in which the amounts of substances causing the generation of the acetal compound during storage are also significantly removed and which thereby can maintain the concentration of the acetal compound such that the concentration is so low as to be equal to or less than 100 ppb by mass even when being passed through an acceleration test with the assumption of long-term storage.

Specific means for solving the problem described above include embodiments below.

A first aspect of the present invention relates to a high-purity isopropyl alcohol having the concentration of an acetal compound having 7 to 12 carbon atoms being equal to or less than 100 ppb by mass, in which, when an acceleration test for performing heating at 80° C. for 4 hours is performed under a nitrogen atmosphere, the amount of increase in the concentration of the acetal compound is 30 or less times a value before the heating, and the concentration of the acetal compound is maintained to be a value equal to or less than 100 ppb by mass.

A second aspect of the present invention relates to the high-purity isopropyl alcohol as described in the first aspect, in which, when an acceleration test for performing heating at 120° C. for 4 hours is performed under a nitrogen atmosphere, the amount of increase in the concentration of the acetal compound is 30 or less times the value before the heating, and the concentration of the acetal compound is maintained to be a value equal to or less than 100 ppb by mass.

A third aspect of the present invention relates to the high-purity isopropyl alcohol as described in the first or second aspect, in which the concentration of an aldehyde compound having 1 to 6 carbon atoms is equal to or less than 1500 ppb by mass.

A fourth aspect of the present invention relates to the high-purity isopropyl alcohol as described in any one of the first to third aspects, in which the concentration of a ketone compound having 3 to 6 carbon atoms is equal to or less than 2000 ppb by mass.

A fifth aspect of the present invention relates to the high-purity isopropyl alcohol as described in any one of the first to fourth aspects, in which a water content is 0.1 to 100 ppm by mass.

A sixth aspect of the present invention relates to the high-purity isopropyl alcohol as described in any one of the first to fifth aspects, in which isopropyl alcohol is obtained by a direct hydration method of propylene.

A seventh aspect of the present invention relates to a method for manufacturing the high-purity isopropyl alcohol as described in the first aspect, the method including: a reduced-pressure distillation step of distilling a low-boiling portion by reduced-pressure distillation so as to perform purification until the concentration of an aldehyde compound having 1 to 6 carbon atoms is reduced to be equal to or less than 1500 ppb by mass; and an atmospheric distillation step of removing a bottom liquid by atmospheric distillation so as to perform purification until the concentration of the acetal compound having 7 to 12 carbon atoms is reduced to be equal to or less than 100 ppb by mass, in which the reduced-pressure distillation step and the atmospheric distillation step are combined to be performed on crude isopropyl alcohol.

An eighth aspect of the present invention relates to the method for manufacturing the high-purity isopropyl alcohol as described in the seventh aspect, in which, in the reduced-pressure distillation step, purification is performed such that the concentration of a ketone compound having 3 to 6 carbon atoms is reduced to be equal to or less than 2000 ppb by mass.

A ninth aspect of the present invention relates to the method for manufacturing the high-purity isopropyl alcohol as described in the seventh or eighth aspect, in which the crude isopropyl alcohol is obtained by a direct hydration method of propylene.

Effects of the Invention

According to the present invention, it is possible to provide a high-purity isopropyl alcohol in which the concentration of an acetal compound that is an impurity is low, in which an increase with time in the concentration of the acetal compound is suppressed and which is excellent in long-term storage stability and a method for manufacturing such a high-purity isopropyl alcohol.

Since the boiling point of the acetal compound is higher than that of isopropyl alcohol, when isopropyl alcohol including the acetal compound is used as a cleaning liquid, this may cause a residue after cleaning and drying. In this regard, in the high-purity isopropyl alcohol of the present invention, the concentration of an acetal compound having 7 to 12 carbon atoms is maintained to be equal to or less than 100 ppb by mass, and thus the high-purity isopropyl alcohol can be particularly suitably used as a cleaning liquid in a semiconductor manufacturing process.

PREFERRED MODE FOR CARRYING OUT THE INVENTION

An embodiment of the present invention will be described in detail below. In the following description including the description of the Examples, "r", "ppm" and "ppb", which represent concentrations, are all based on mass.

<High-Purity Isopropyl Alcohol>

In a high-purity isopropyl alcohol according to the present embodiment, the concentration of an acetal compound having 7 to 12 carbon atoms is equal to or less than 100 ppb, and when an acceleration test for performing heating at 80° C. for 4 hours is performed under a nitrogen atmosphere, the amount of increase in the concentration of the acetal compound is 30 or less times a value before the heating, and the concentration of the acetal compound is maintained to be a value equal to or less than 100 ppb.

Here, the concentration of the acetal compound (the concentration of the total of the acetal compound), the concentration of an aldehyde compound which will be described later (the concentration of the total of the aldehyde compound), the concentration of a ketone compound which will be described later (the concentration of the total of the ketone compound) and a water content which will be described later are concentrations or amounts with reference to the total of the high-purity isopropyl alcohol. These concentrations or amounts are measured by a measurement method which will be described later.

The high-purity isopropyl alcohol according to the present embodiment means an isopropyl alcohol in which when its concentration excepting water is indicated by mass spectrometry (GC/MS) using gas chromatography, the concentration of the isopropyl alcohol is equal to or greater than 99.99% and preferably equal to or greater than 99.999%.

(Impurity: Acetal Compound)

The acetal compound in the present embodiment is a compound represented by formula (1) below, and is generated by the condensation of an aldehyde compound having 1 to 6 carbon atoms and a ketone compound having 3 to 6 carbon atoms with alcohol under an acid catalyst or an alkali catalyst. For example, an acetal compound having 9 carbon atoms is generated from propionaldehyde and isopropyl alcohol.

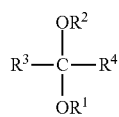

(1)

In the formula, $R^1$ and $R^2$ each independently represent an alkyl group. $R^3$ and $R^4$ each independently represent a hydrogen atom or an alkyl group.

Specific examples of the acetal compound having 7 to 12 carbon atoms include acetone diethyl acetal, acetone diisopropyl acetal, acetaldehyde diisopropyl acetal, propionaldehyde diisopropyl acetal, butyraldehyde diisopropyl acetal, valeraldehyde diisopropyl acetal, hexanal diisopropyl acetal, acetone diisopropyl acetal, butanone diisopropyl acetal, 2-pentanone diisopropyl acetal, 2-methyl-3-pentanone diisopropyl acetal and the like.

In the high-purity isopropyl alcohol according to the present embodiment, the concentration of the total of the acetal compounds as described above is equal or less than 100 ppb, preferably equal or less than 50 ppb and more preferably equal or less than 20 ppb. When the high-purity isopropyl alcohol according to the present embodiment is used as a cleaning liquid in a semiconductor manufacturing process, the more the acetal compound, whose boiling point is higher than isopropyl alcohol, is minimized (that is, preferably closer to 0 ppb), the more preferable in that a residue is prevented from being left in a material to be treated after cleaning and drying. However, with consideration given to the industrial manufacturing, the storage and the transportation of isopropyl alcohol, the lower limit value of the concentration of the total of the acetal compound is preferably 0.1 ppb and more preferably 0.5 ppb.

In the high-purity isopropyl alcohol according to the present embodiment, not only is the concentration of the acetal compound having 7 to 12 carbon atoms so low as to be equal to or less than 100 ppb, but also the amounts of substances causing the generation of the acetal compound during storage are significantly reduced, and when the acceleration test for performing heating at 80° C. for 4 hours is performed under a nitrogen atmosphere, the amount of increase in the concentration of the acetal compound is 30 or less times the value before the heating, and the concentration of the acetal compound is maintained to be a value equal to or less than 100 ppb. Here, the acceleration test described above is substantially comparable to the severity against the increasing action of the acetal compound received by isopropyl alcohol when the isopropyl alcohol is stored under room temperature (25° C.) in the dark for 6 months.

Preferably, in the high-purity isopropyl alcohol according to the present embodiment, when an acceleration test for performing heating at 120° C. for 4 hours is performed under a nitrogen atmosphere, the amount of increase in the concentration of the acetal compound is 30 or less times the value before the heating, and the concentration of the acetal compound is maintained to be a value equal to or less than 100 ppb. The property in which an increase in the amount of acetal compound is suppressed even under the harsher conditions described above means that even when the isopropyl alcohol is passed through logistics and long-term storage under high temperature in summer, the concentration of the acetal compound is suppressed to be low, and thus it is possible to greatly improve a defect caused by a residue when the isopropyl alcohol is used for the cleaning application of an electronic device such as a semiconductor device.

In the present embodiment, the amount of increase in the concentration of the acetal compound after the acceleration test is preferably 10 or less times the value before the heating, and more preferably 5 or less times the value.

The concentration of the acetal compound after the acceleration test is specifically measured by the following method. Specifically, 10 mL of the high-purity isopropyl alcohol is put into a stainless steel (SUS) pipe of about 20 ml, and nitrogen is supplied at a rate of 100 mL/minute for 30 minutes so as to perform deoxidizing. After the deoxidizing, the stainless steel pipe is hermetically sealed such that oxygen is prevented from entering the stainless steel pipe, and the SUS pipe is heated with an oil bath of 80° C. or 120° C. for 4 hours. Then, after the completion of the acceleration test, the concentration of the acetal compound in the isopropyl alcohol within the SUS pipe is measured.

The property in which the amount of acetal compound is prevented from being greatly increased in the isopropyl alcohol even by the harsh acceleration test as described above is achieved by reducing the amount of aldehyde compound having 1 to 6 carbon atoms or the amount of aldehyde compound described above and the amount of ketone compound having 3 to 6 carbon atoms. It can be thought that the acetal compound is generated by the aldehyde compound having 1 to 6 carbon atoms or the aldehyde compound described above and the ketone compound having 3 to 6 carbon atoms which are inevitably included at the time of manufacturing of the isopropyl alcohol, and is increased with time after the manufacturing. Hence, the amounts of these specific low-boiling point organic impurities are significantly reduced, and thus the property in the acceleration test described above is satisfied.

(Impurity: Aldehyde Compound and Ketone Compound)

In the present embodiment, the concentration of the total of the aldehyde compound having 1 to 6 carbon atoms included in the high-purity isopropyl alcohol is preferably equal to or less than 1500 ppb, more preferably equal to or less than 500 ppb and further preferably equal to or less than 150 ppb in that an increase in the amount of acetal compound is suppressed. It can be thought that when the lower limit value of the concentration of the aldehyde compound is minimized, the generation of the acetal compound can be suppressed, and thus the lower limit value is preferably 0 ppb. However, with consideration given to the industrial production of the isopropyl alcohol, the lower limit value is preferably 1 ppb, more preferably 10 ppb and further preferably 50 ppb.

In the present embodiment, the concentration of the total of the ketone compound having 3 to 6 carbon atoms included in the high-purity isopropyl alcohol is preferably equal to or less than 2000 ppb, more preferably equal to or less than 1000 ppb and further preferably equal to or less than 500 ppb in that an increase in the amount of acetal compound is suppressed. It can be thought that when the lower limit value of the concentration of the ketone compound is minimized, the generation of the acetal compound can be suppressed, and thus the lower limit value is preferably 0 ppb. However, with consideration given to the industrial production of the isopropyl alcohol, the lower limit value is preferably 10 ppb, more preferably 50 ppb and further preferably 100 ppb. The ketone compound is unlikely to change into the acetal compound as compared with the aldehyde compound, and thus even when they have the same concentration, the amount of acetal compound generated is normally equal to or lower than one tenth.

In the present embodiment, the aldehyde compound and the ketone compound are preferably prevented from coexisting, and even when they coexist, the concentrations thereof are preferably low.

Conventionally, it is thought that even when an aldehyde compound and a ketone compound (in particular, the aldehyde compound) are included in isopropyl alcohol, these impurities often have a boiling point lower than that of isopropyl alcohol, and that thus even when they are used in a cleaning liquid, an adverse influence is not exerted. However, it was found from the study of the present inventors that the concentrations of these compounds, in particular, the concentration of the aldehyde compound is set to fall within the range described above, thus an increase in the amount of acetal compound is suppressed and even when the acceleration test is performed, it is possible to easily control the concentration of the acetal compound such that the concentration is equal to or less than 100 ppb. For the same reason, the concentration of the ketone compound is preferably set to fall within the range described above.

Since as described above, the aldehyde compound easily generates the acetal compound as compared with the ketone compound, it is particularly important to control the range of the concentration of the aldehyde compound. Specific examples of the aldehyde compound having 1 to 6 carbon atoms include formaldehyde, acetaldehyde, propionaldehyde, butyraldehyde, valeraldehyde, 2-methylbutyraldehyde, isovaleraldehyde, hexanal and the like.

Specific examples of the ketone compound having 3 to 6 carbon atoms include acetone, methyl ethyl ketone, diethyl ketone, methyl propyl ketone, methyl isopropyl ketone, 4-methyl-2-pentanone, 3-methyl-2-pentanone, 2-methyl-3-pentanone and the like.

Isopropyl alcohol is normally manufactured by an acetone reduction method of reducing acetone to synthesize isopropyl alcohol, an indirect hydration method of using concentrated sulfuric acid to esterify propylene and thereafter performing hydrolysis, a direct hydration method of utilizing a catalyst to directly hydrate propylene or the like. Among them, in the present embodiment, it is preferable to target an isopropyl alcohol that is obtained by using a method, raw materials and the like in which the aldehyde compound is easily generated. Specifically, it is preferable to target an isopropyl alcohol manufactured by the direct hydration method.

The isopropyl alcohol manufactured by the direct hydration method contains, before being purified, more than 100 ppb of the acetal compound having 7 to 12 carbon atoms, and mostly contains more than 300 ppb thereof. The isopropyl alcohol also contains more than 1500 ppb of the aldehyde compound having 1 to 6 carbon atoms, and mostly contains more than 3000 ppb thereof. The isopropyl alcohol further contains more than 2000 ppb of the ketone compound having 3 to 6 carbon atoms, and mostly contains more than 4000 ppb thereof.

Examples of the factor in the aldehyde compound having 1 to 6 carbon atoms and/or the ketone compound having 3 to 6 carbon atoms being included in isopropyl alcohol include "an impurity included in propylene/acetone serving as raw materials of the isopropyl alcohol", "a by-product of the synthetic reaction of isopropyl alcohol", "an alcohol compound included in isopropyl alcohol after being manufactured" and the like.

By these factors, in general, the aldehyde compound having 1 to 6 carbon atoms and the ketone compound having 3 to 6 carbon atoms are inevitably mixed in isopropyl alcohol manufactured industrially.

For example, ethylene included as an impurity in propylene serving as a raw material is oxidized to generate ethanol. It can be thought that ethanol is oxidized by the influence of dissolved oxygen included in isopropyl alcohol to change into acetaldehyde and is included as the aldehyde compound in the isopropyl alcohol. It can be thought that alcohols such as 1-propanol, 1-butanol, 2-butanol, 2-pentanol, 4-methyl-2-pentanol, 3-methyl-2-pentanol and 2-methyl-3-pentanol inevitably exist as by-products of reactions, and that thus as the oxidation reaction products of the alcohols described above, propionaldehyde, butyraldehyde, methyl ethyl ketone, methyl propyl ketone, 4-methyl-2-pentanone, 3-methyl-2-pentanone, 2-methyl-3-pentanone and the like are generated.

As described above, the aldehyde compound and the ketone compound are impurities which are generated as the by-products of reactions or generated by an oxidation reaction and the like in a reaction step, a purification step and during storage, and large amounts thereof are included in isopropyl alcohol, with the result that the concentration ranges thereof have not so far been strictly controlled.

However, it can be thought by the study of the present inventors that, for example, when the aldehyde compound is included in isopropyl alcohol, the isopropyl alcohol and the aldehyde compound react with each other as indicated by a reaction formula below, and that thus the amount of acetal compound is increased with time. The reaction formula below illustrates a case where in the acetal compound represented by formula (1) above, $R^1$ and $R^2$ are isopropyl groups.

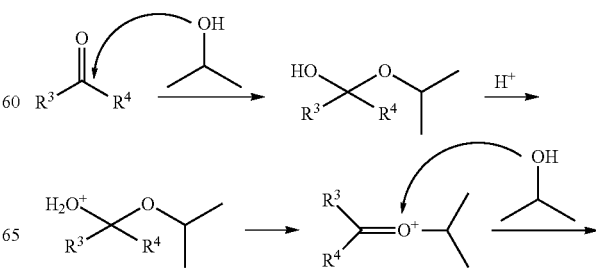

-continued

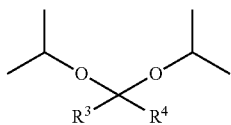

According to the above reaction formula, the concentration of acetaldehyde included in isopropyl alcohol is controlled, and thus an increase in the amount of acetal compound having 8 carbon atoms can be suppressed.

In addition, aldehyde compounds having different carbon atoms other than acetaldehyde are included in isopropyl alcohol, and thus, for example, in a reaction between propionaldehyde having 3 carbon atoms and isopropyl alcohol, the amount of acetal compound having 9 carbon atoms is increased with time.

Hence, it is estimated that the concentration of the aldehyde compound having 1 to 6 carbon atoms included in isopropyl alcohol is controlled to be within a specific range, and thus it is possible to suppress an increase with time in the amount of acetal compound. When $R^3$ and $R^4$ in formula (1) above are alkyl groups, though the impurity serving as a raw material is the ketone compound, it can be thought that even in this case, the amount of acetal compound is naturally increased by the same reaction mechanism.

There is a case where aldehyde compounds included as impurities are condensed together so as to generate high-boiling point organic substances during storage, and these condensates may be residues after cleaning and drying. Hence, the concentration of the aldehyde compound having 1 to 6 carbon atoms is controlled to be within a specific range, and thus it is also possible to prevent the condensation of aldehyde compounds together.

(Other Impurities)

The high-purity isopropyl alcohol according to the present embodiment may include other impurities which are inevitably mixed therein during manufacturing. Examples of the impurities which are inevitably mixed therein include water, an organic impurity, an inorganic impurity and the like. Among them, the organic impurity is not separated in a step of distilling isopropyl alcohol so as to be mixed therein.

(Water)

A water content in the high-purity isopropyl alcohol according to the present embodiment is preferably 0.1 to 100 ppm. Water in the isopropyl alcohol is considered to cause a residue or a water mark after cleaning and drying, and may act as a catalyst. Hence, the water content is preferably equal to or less than 100 ppm. On the other hand, since the reaction in which the acetal compound is generated is a dehydration reaction, with consideration given to chemical equilibrium, it can be thought that the generation of the acetal compound can be more suppressed if water exists in the isopropyl alcohol.

Hence, the water content is preferably equal to or greater than 0.1 ppm. In terms of the use of the high-purity isopropyl alcohol as a cleaning liquid and the suppression of generation of the acetal compound, the water content is more preferably 1 to 50 ppm and further preferably 3 to 25 ppm.

Furthermore, the total mass of the aldehyde compound and the ketone compound and the water content included in the high-purity isopropyl alcohol according to the present embodiment preferably satisfy a relationship below.

Specifically, a rate p represented in formula (I) below is preferably 0.001 to 1 and more preferably 0.01 to 0.1.

$$p=\text{(total mass of aldehyde compound and ketone compound)/(water content)} \quad \text{(I)}$$

As described above, since the reaction in which the acetal compound is generated is a dehydration reaction, with consideration given to chemical equilibrium, it can be thought that the generation of the acetal compound can be suppressed by water existing in isopropyl alcohol. On the other hand, it can be thought that isopropyl alcohol is oxidized by water existing in the isopropyl alcohol so as to supply the aldehyde compound and the ketone compound serving as the raw materials of the acetal compound. Hence, it can be thought that when the rate p described above exceeds 1, the amount of water is decreased, and that thus the generation of the acetal compound tends to be increased. On the other hand, when the rate p described above is less than 0.001, the amount of aldehyde compound tends to be increased, and thus the amount of acetal compound may be finally increased.

For the reason described above, it can be thought that in the high-purity isopropyl alcohol according to the present embodiment, the rate p described above is controlled to be within a range of 0.001 to 1, and that thus the generation of the acetal compound can be more suppressed.

The water content is also controlled, and thus the high-purity isopropyl alcohol according to the present embodiment is more excellent in long-term storage stability, with the result that the high-purity isopropyl alcohol can be transported and stored for a long time. For example, the high-purity isopropyl alcohol can be suitably used as a cleaning liquid in a semiconductor manufacturing process.

(Other Impurity: Free Acid)

It is estimated that a free acid acts as a catalyst in the generation of the acetal compound. Hence, the concentration of an organic acid in the high-purity isopropyl alcohol according to the present embodiment is preferably equal to or less than 10 ppm, more preferably equal to or less than 100 ppb and further preferably equal to or less than 10 ppb. Although the lower limit value thereof is preferably minimized, with consideration given to the industrial manufacturing, the storage and the transportation, the lower limit value is normally equal to or greater than 0.1 ppb.

<Method for Manufacturing High-Purity Isopropyl Alcohol>

The high-purity isopropyl alcohol according to the present embodiment may be manufactured by any method as long as the properties described above are satisfied. As a preferred manufacturing method, a method is mentioned in which a reduced-pressure distillation step of distilling a low-boiling portion by reduced-pressure distillation so as to perform purification until the concentration of an aldehyde compound having 1 to 6 carbon atoms is reduced to be equal to or less than 1500 ppb by mass and an atmospheric distillation step of removing a bottom liquid by atmospheric distillation so as to perform purification until the concentration of an acetal compound having 7 to 12 carbon atoms is reduced to be equal to or less than 100 ppb by mass are combined to be performed on crude isopropyl alcohol.

As described above, the present inventors have found for the first time that the acetal compound having 7 to 12 carbon atoms exists as an impurity in isopropyl alcohol. Although it is known as disclosed in Patent Document 3 and the like that distillation purification is performed when isopropyl alcohol is manufactured, since the acetal compound described above is not recognized as a harmful organic impurity which needs to be removed, an operation of reducing the amount of acetal compound to a minute amount beyond the degree of normal distillation is not performed. It is not known that the aldehyde compound having 1 to 6 carbon atoms exists in isopropyl alcohol, and it is also not known that the ketone compound having 3 to 6 carbon atoms except acetone exists in isopropyl alcohol. It is further not known that the aldehyde compound having 1 to 6 carbon atoms and the ketone compound having 3 to 6 carbon atoms serve as substances causing the generation of the acetal compound. Hence, an operation of reducing the amounts of these causal substances to minute amounts beyond the degree of normal distillation is not performed.

Moreover, the aldehyde compound having 1 to 6 carbon atoms is highly compatible with isopropyl alcohol, and thus it is difficult to significantly distill it by distillation under normal pressure. Hence, even when crude isopropyl alcohol is repeatedly subjected to atmospheric distillation, it is difficult to lower the concentration of the aldehyde compound to 1500 ppb or less. In particular, butyraldehyde is remarkably poor in separation performance with isopropyl alcohol in atmospheric distillation, and thus it is significantly difficult to lower the concentration thereof. Likewise, the ketone compound having 3 to 6 carbon atoms is highly compatible with isopropyl alcohol, and thus it is difficult to lower the concentration of the ketone compound to 2000 ppb or less by atmospheric distillation. In particular, methyl propyl ketone is remarkably poor in separation performance with isopropyl alcohol, and thus it is significantly difficult to lower the concentration thereof.

By contrast, it was found that when isopropyl alcohol is subjected to reduced-pressure distillation, both the aldehyde compound having 1 to 6 carbon atoms and the ketone compound having 3 to 6 carbon atoms can be removed highly efficiently. In other words, in the reduced-pressure distillation step, the low-boiling portion is distilled, and thus it is possible to lower the concentrations of the aldehyde compound having 1 to 6 carbon atoms and the ketone compound having 3 to 6 carbon atoms to the concentrations described above.

The pressure of reduced-pressure distillation is preferably equal to or less than 20 kPa, more preferably equal to or less than 10 kPa and further preferably equal to or less than 5 kPa. In terms of the hermeticity and economy of a device, the lower limit of the pressure is preferably equal to or greater than 1 kPa and more preferably equal to or greater than 3 kPa.

As a distillation tower for performing reduced-pressure distillation, a distillation tower known in this field can be used without limitation, and as preferred examples, a plate tower and a packed tower can be mentioned. Reduced-pressure distillation is intended for reducing the substances (the aldehyde compound having 1 to 6 carbon atoms and the ketone compound having 3 to 6 carbon atoms) causing the generation of the acetal compound, and since distillation at normal pressure and distillation at reduced pressure are performed separately, a small number of plates can be set. Although the number of plates in the plate tower or the corresponding number of plates in the distillation tower obtained by conversion to the plate tower is not limited, an excessive number thereof increases the cost of distillation facilities, and thus 2 to 30 plates are preferable, 3 to 20 plates are more preferable and 5 to 10 plates are further preferable.

Although a reflux ratio in reduced-pressure distillation is not limited, an excessive reflux ratio increases the cost of the distillation facilities, and thus the reflux ratio is preferably 1 to 100, more preferably 5 to 50 and further preferably 10 to 20. As the plate tower, a cross-flow tray, a shower tray and the like can be used. Examples of a filling material when the packed tower is used include known filling materials such as a Raschig ring and a Lessing ring. The material of the tower and the material of the filling material are not limited, and various types of metals and various types of resins such as iron, SUS, hastelloy, borosilicate glass, quartz glass and fluororesin (for example, polytetrafluoroethylene) can be used.

In the method for manufacturing the high-purity isopropyl alcohol described above, it is essential to remove a bottom liquid in the atmospheric distillation step so as to reduce the concentration of the acetal compound having 7 to 12 carbon atoms to 100 ppb or less. The acetal compound having 7 to 12 carbon atoms can be significantly removed only by atmospheric distillation.

Although the number of plates of the plate tower in the distillation tower or the corresponding number of plates in the distillation tower obtained by conversion to the plate tower is not limited, the number thereof is preferably 10 to 300. Although a reflux ratio in atmospheric distillation is not limited, the reflux ratio is preferably 0.5 to 50 and more preferably 1 to 10. The other conditions of atmospheric distillation are the same as those described in reduced-pressure distillation.

As long as the reduced-pressure distillation step and the atmospheric distillation step are combined to be performed, the order in which they are performed is not limited, and the reduced-pressure distillation step may first be performed and then the atmospheric distillation step may be performed and vice versa. In terms of the elution of the materials used and the mixing of the impurities at the time of reduced-pressure distillation, it is preferable to first perform the reduced-pressure distillation step and then perform the atmospheric distillation step.

In the reduced-pressure distillation step, not only is the low-boiling portion distilled to lower the concentration of the aldehyde compound having 1 to 6 carbon atoms (furthermore, the ketone compound having 3 to 6 carbon atoms), but also the bottom liquid of a high-boiling portion may be removed. In this case, the purified isopropyl alcohol is preferably removed from the side portion of the distillation tower. Even when the bottom liquid of the high-boiling portion is removed in the reduced-pressure distillation step as described above, the acetal compound having 7 to 12 carbon atoms cannot be significantly removed, with the result that it is necessary to perform the atmospheric distillation step.

Furthermore, in the atmospheric distillation step, the bottom liquid is removed, and thus not only is the concentration of the acetal compound having 7 to 12 carbon atoms lowered, but also the low-boiling portion may be distilled. In this case, the high-purity isopropyl alcohol is preferably removed from the side portion of the distillation tower. Even when the low-boiling portion is distilled in the atmospheric distillation step as described above, the aldehyde compound having 1 to 6 carbon atoms (furthermore, the ketone compound having 3 to 6 carbon atoms) cannot be significantly removed, with the result that it is necessary to perform the reduced-pressure distillation step.

EXAMPLES

Although the present invention will be more specifically described below using Examples, the present invention is not limited to these Examples.

The analytical and quantitative methods of the impurities and the like will first be described.

(Measurement Method of Acetal Compound; Qualitative Analysis)

An acetal compound included in isopropyl alcohol was measured with GC-MS under measurement conditions shown below.

—Measurement Conditions—
Device: 7890A/5975C (made by Agilent Technologies, Inc.)
Analytical column: SUPELCO WAX-10 (60 m×0.25 mm, 0.25 μm)
Column temperature: 35° C. (held for 2 minutes)→temperature rise at 5° C./minute→100° C.→temperature rise at 10° C./minute→240° C. (held for 6 minutes)
Carrier gas: helium
Carrier gas flow rate: 2 mL/minute
Injection port temperature: 240° C.
Sample injection method: pulsed splitless method
Pulse pressure at time of injection: 90 psi (2 minutes)
Split vent flow rate: 50 mL/minute (2 minutes)
Use of gas saver: 20 mL/minute (5 minutes)
Transfer line temperature: 240° C.
Ion source, quadrupole temperature: 230° C., 150° C.
Scan ion: m/Z=25 to 250

When isopropyl alcohol was not concentrated, if in a chart obtained according to the conditions described above, no peak was detected in a region where a holding time was long as compared with isopropyl alcohol, the concentration of the acetal compound can be evaluated to be equal to or less than 500 ppb, which is a detection lower limit.

(Measurement Method of Acetal Compound; Quantitative Analysis)

When a peak was confirmed in a chart obtained according to the method of the qualitative analysis described above, a library search was made from the mass spectrum of the peak, and thus a structure was identified. Then, the standard substance of the identified acetal compound was prepared, a comparison was made with the pre-quantified peak area of the standard substance and thus the concentration of the acetal compound detected by the qualitative analysis was quantified by a selective ion detection method (SIM).

—SIM Monitor Ion—
Group 1 start time: 12.7 minutes, m/Z: 101, 131, 145 (Duel 60)

(Measurement Method of Aldehyde Compound; Qualitative Analysis)

An aldehyde compound included in isopropyl alcohol was measured with GC-MS under measurement conditions shown below.

—Measurement Conditions—
Device: 7890A/5975C (made by Agilent Technologies, Inc.)
Analytical column: SUPELCO WAX-10 (60 m×0.25 mm, 0.25 μm)
Column temperature: 35° C. (held for 2 minutes)→temperature rise at 5° C./minute→100° C.→temperature rise at 10° C./minute→240° C. (held for 6 minutes)
Carrier gas: helium
Carrier gas flow rate: 2 mL/minute
Injection port temperature: 240° C.
Sample injection method: split method
Split ratio: 1:10
Transfer line temperature: 240° C.
Ion source, quadrupole temperature: 230° C., 150° C.
Scan ion: m/Z=25 to 250

When isopropyl alcohol was not concentrated, if in a chart obtained according to the conditions described above, no peak was detected in a region where a holding time was short as compared with isopropyl alcohol, the concentration of the aldehyde compound can be evaluated to be equal to or less than 5000 ppb, which is a detection lower limit.

(Measurement Method of Aldehyde Compound; Quantitative Analysis)

When a peak was confirmed in a chart obtained according to the method of the qualitative analysis described above as in the quantitative analysis of the acetal compound, a library search was made from the mass spectrum of the peak, and thus a structure was identified. Then, the standard substance of the identified aldehyde compound was prepared, a comparison was made with the pre-quantified peak area of the standard substance and thus the concentration of the aldehyde compound detected by the qualitative analysis was quantified by the selective ion detection method (SIM).

—SIM Monitor Ion—
m/Z: 29 (acetaldehyde analysis)
m/Z: 58 (acetone, propionaldehyde analysis)
m/Z: 72 (butyraldehyde, methyl ethyl ketone analysis)

(Measurement Method of Water Content)
Device: Karl Fischer Water Analyzer AQ-7 (made by HIRANUMA Co., Ltd.)
Method: 0.25 g of a measurement sample and 0.75 g of dehydrated acetonitrile were mixed in a glove box whose dew point was equal to or less than −80° C. 0.5 g of the mixed solution was collected with a Terumo Syringe (product name, 2.5 mL) sufficiently dried in the glove box and a measurement was made with the Karl Fischer Water Analyzer.

Example 1

Isopropyl alcohol for electronic industry made by Tokuyama Corporation (in which a bottom liquid was removed by atmospheric distillation) was prepared, and a distillation operation described below was performed.

(Distillation Operation)

A flask of 2 L was put into a water bath, and a packed tower whose length was 2 m and in which glass beads were put was installed. 2 L of isopropyl alcohol was put into the flask. The pressure was reduced to 5 kPa, and distillation was performed under conditions in which the water bath had a temperature of 50° C., the temperature of a tower top was 15 to 25° C. and the temperature of a cooler was −5 to 0° C. When after the distillation operation, a measurement was made according to the measurement method of the aldehyde compound described above, as the aldehyde compound, acetaldehyde, propionaldehyde and butyraldehyde were detected. The concentration of the total of acetaldehyde, propionaldehyde and butyraldehyde was equal to or less than 100 ppb. It can be thought that acetaldehyde, propionaldehyde and butyraldehyde were discharged to the outside of the system without being condensed.

Furthermore, a water content included in the isopropyl alcohol purified by the distillation operation was 5 ppm. A free acid (calculated as acetic acid) included in the isopropyl alcohol was 2 ppm.

Then, in order to check the storage stability of the isopropyl alcohol purified by the distillation operation, an acceleration test was performed under conditions shown below.

(Acceleration Test)

10 mL of a sample which was obtained by distillation and in which the concentration of the total of acetaldehyde, propionaldehyde and butyraldehyde was equal to or less than 100 ppb was put into a SUS pipe of about 20 mL, and nitrogen was supplied at a rate of 100 mL/minute for 30 minutes so as to perform deoxidizing. After the deoxidizing, the SUS pipe was hermetically sealed such that oxygen was prevented from entering the SUS pipe. The SUS pipe was heated with an oil bath of 120° C. for 4 hours. When after the completion of the acceleration test, a measurement was made according to the measurement method of the acetal compound described above, the concentration of the acetal compound was 20 ppb (table 1).

As described above, in the isopropyl alcohol in which the concentration of the total of acetaldehyde, propionaldehyde and butyraldehyde was reduced to 100 ppb or less, the concentration of the acetal compound was 20 ppb even after the acceleration test, and thus excellent long-term storage stability was shown.

Comparative Example 1

Isopropyl alcohol for industry made by Tokuyama Corporation was prepared, the same acceleration test as in Example 1 was performed except that acetaldehyde, propionaldehyde and butyraldehyde were not distilled, and the evaluation of the acetal compound was performed. Consequently, the concentration of the acetal compound was increased to 2000 ppb (table 1).

As described above, in the isopropyl alcohol in which the concentration of acetaldehyde, propionaldehyde and butyraldehyde was not reduced, as a result of the acceleration test, the concentration of the acetal compound reached 2000 ppb, and thus long-term storage stability was poor.

TABLE 1

| | Water content (ppm) | Total concentration of aldehyde compound (ppm) | Total concentration of acetal compound (ppm) | Total concentration of acetal compound after acceleration test of 120° C. (ppm) |
|---|---|---|---|---|
| Example 1 | 5 | 0.1 or less | 0.02 | 0.02 |
| Comparative Example 1 | 5 | 5 | 0.02 | 2 |

Example 2

(Manufacturing of Crude Isopropyl Alcohol)

As propylene serving as a raw material, propylene which included, as impurities, 39972 ppm of propane, 20 ppm of ethane, 8 ppm of butene, 0.1 ppm or less of pentene and 0.1 ppm or less of hexene was prepared. As water serving as a raw material, water whose pH was adjusted to be 3.0 by the addition of phosphor tungstic acid serving as an acid catalyst was prepared. The water heated to 110° C. was charged into a reactor having an internal volume of 10 L at a supply rate of 18.4 kg/h (20 L/h because the density was 920 kg/m$^3$), and the propylene was charged thereinto at a supply rate of 1.2 kg/h.

A reaction temperature within the reactor was set to 280° C., a reaction pressure was set to 250 atm and the propylene and the water were made to react with each other so as to obtain isopropyl alcohol. A reaction product including the generated isopropyl alcohol was cooled to 140° C., the pressure was reduced to 18 atm and thus the propylene dissolved in the water included in the reaction product was recovered as gas. The recovered propylene was charged into a recovery drum for propylene in order to be recycled as the raw material. Here, a conversion rate of the supplied propylene was 84.0%, and a selection rate of the propylene to the isopropyl alcohol was 99.2%.

Then, dehydration was performed by distillation, and thus crude isopropyl alcohol in which the concentration of isopropyl alcohol was 99 was obtained. For the obtained crude isopropyl alcohol, the concentrations of the acetal compound, the aldehyde compound and the ketone compound were measured, and the results thereof are shown in table 2.

TABLE 2

| Concentrations in crude isopropyl alcohol (ppb) | | |
|---|---|---|
| C7-C12 acetal compound | C8 acetal | 200 |
| | C9 acetal | 200 |
| | Other acetals | 20 |
| | Acetal compound total | 420 |
| C1-C6 aldehyde compound | Acetaldehyde | 1000 |
| | Propionaldehyde | 2000 |
| | Butyraldehyde | 500 |
| | Aldehyde compound total | 3500 |
| C3-C6 ketone compound | Acetone | 500 |
| | 2-Pentanone | 1000 |
| | 3-Methyl-2-pentanone | 500 |
| | Ketone compound total | 2000 |

(Purification of Crude Isopropyl Alcohol)

A flask of 2 L was put into a water bath, and a packed tower (the corresponding number of plates by conversion to the plate tower was 10) whose length was 2 m and in which glass beads were put was prepared. 2 L of the crude isopropyl alcohol was put into the flask. Reduced-pressure distillation was performed under conditions in which the pressure was 20 kPa, a reflux ratio was 3, the temperature of the water bath was 70° C., the temperature of a tower top was 35 to 45° C. and the temperature of a cooler was −5 to 0° C., with the result that a low-boiling portion was distilled. Then, as in the same manner as described above, a flask of 2 L was put into a water bath, and a distillation tower (the corresponding number of plates by conversion to the plate tower was 20) whose length was 3 m and in which glass beads were put was prepared. The isopropyl alcohol obtained by reduced-pressure distillation was put into the flask. Atmospheric distillation was performed under conditions in which a reflux ratio was 3, the temperature of an oil bath was 120° C., the temperature of a tower top was 82° C. and the temperature of a cooler was 25° C. When the concentration of the isopropyl alcohol in a distilled liquid was measured with GC/MS, the concentration of the isopropyl alcohol excepting water was so highly pure as to be equal to or greater than 99.999%. For the obtained high-purity isopropyl alcohol, the concentrations of the acetal compound, the aldehyde compound and the ketone compound were measured, and the results thereof are shown in tables 3 to 5. For the obtained high-purity isopropyl alcohol, a water content was measured, and the result thereof is also shown in table 3.

(Acceleration Test)

On the high-purity isopropyl alcohol obtained as described above, in the same manner as in Example 1, an acceleration test at a heating temperature of 80° C. was performed, and the evaluation of the acetal compound was performed. Consequently, the concentration of the acetal compound was 90 ppb (table 6). Aside from this test, an SUS pipe in which the high-purity isopropyl alcohol was stored was stored under room temperature (25° C.) for 6 months, and the acetal compound was measured, with the result that the concentration thereof was 85 ppb. Hence, it can be confirmed that the acceleration test at 80° C. is substantially comparable to the severity against the increasing action of the acetal compound received by isopropyl alcohol when the isopropyl alcohol is stored under room temperature (25° C.) in the dark for 6 months.

Furthermore, when the same acceleration test (except that the heating temperature in the oil bath of the SUS pipe was changed to 120° C.) was performed, the concentration of the acetal compound was 350 ppb (table 7).

Example 3

In the same manner as in Example 2 except that the conditions of reduced-pressure distillation in Example 2 (purification of crude isopropyl alcohol) were changed to conditions in which the pressure was 10 kPa, the reflux ratio was 3, the temperature of the water bath was 70° C., the temperature of the tower top was 28 to 38° C. and the temperature of the cooler was −5 to 0° C., a high-purity isopropyl alcohol in which the concentration of isopropyl alcohol excepting water was equal to or greater than 99.999% was manufactured. For the obtained high-purity isopropyl alcohol, the concentrations of the acetal compound, the aldehyde compound and the ketone compound were measured, and the results thereof are shown in tables 3 to 5. For the obtained high-purity isopropyl alcohol, a water content was measured, and the result thereof is also shown in table 3.
(Acceleration Test)

On the high-purity isopropyl alcohol obtained as described above, in the same manner as in Example 1, acceleration tests under temperature conditions of 80° C. and 120° C. were performed, and the evaluation of the acetal compound was performed. Consequently, the concentration of the acetal compound was 40 ppb (table 6) at 80° C. and was 85 ppb (table 7) at 120° C.

Example 4

In the same manner as in Example 2 except that the conditions of reduced-pressure distillation in Example 2 (purification of crude isopropyl alcohol) were changed to conditions in which the pressure was 5 kPa, the reflux ratio was 6, the temperature of the water bath was 50° C., the temperature of the tower top was 15 to 25° C. and the temperature of the cooler was −5 to 0° C., a high-purity isopropyl alcohol in which the concentration of isopropyl alcohol excepting water was equal to or greater than 99.999% by mass was manufactured. For the obtained high-purity isopropyl alcohol, the concentrations of the acetal compound, the aldehyde compound and the ketone compound were measured, and the results thereof are shown in tables 3 to 5. For the obtained high-purity isopropyl alcohol, a water content was measured, and the result thereof is also shown in table 3.
(Acceleration Test)

On the high-purity isopropyl alcohol obtained as described above, in the same manner as in Example 1, acceleration tests under temperature conditions of 80° C. and 120° C. were performed, and the evaluation of the acetal compound was performed. Consequently, the concentration of the acetal compound was 19 ppb (table 6) at 80° C. and was 27 ppb (table 7) at 120° C.

Example 5

In the same manner as in Example 2 except that the conditions of reduced-pressure distillation in Example 2 (purification of crude isopropyl alcohol) were changed to conditions in which the pressure was 5 kPa, the reflux ratio was 9, the temperature of the water bath was 50° C., the temperature of the tower top was 15 to 25° C. and the temperature of the cooler was −5 to 0° C., a high-purity isopropyl alcohol in which the concentration of isopropyl alcohol excepting water was equal to or greater than 99.999% by mass was manufactured. For the obtained high-purity isopropyl alcohol, the concentrations of the acetal compound, the aldehyde compound and the ketone compound were measured, and the results thereof are shown in tables 3 to 5. For the obtained high-purity isopropyl alcohol, a water content was measured, and the result thereof is also shown in table 3.
(Acceleration Test)

On the high-purity isopropyl alcohol obtained as described above, in the same manner as in Example 1, acceleration tests under temperature conditions of 80° C. and 120° C. were performed, and the evaluation of the acetal compound was performed. Consequently, the concentration of the acetal compound was 11 ppb (table 6) at 80° C. and was 15 ppb (table 7) at 120° C.

Example 6

In the same manner as in Example 2 except that the conditions of atmospheric distillation in Example 2 (purification of crude isopropyl alcohol) were changed to conditions in which the number of plates was 10, the reflux ratio was 1, the temperature of the oil bath was 120° C., the temperature of the tower top was 82° C. and the temperature of the cooler was 25° C., a high-purity isopropyl alcohol in which the concentration of isopropyl alcohol excepting water was equal to or greater than 99.999% by mass was manufactured. For the obtained high-purity isopropyl alcohol, the concentrations of the acetal compound, the aldehyde compound and the ketone compound were measured, and the results thereof are shown in tables 3 to 5. For the obtained high-purity isopropyl alcohol, a water content was measured, and the result thereof is also shown in table 3.
(Acceleration Test)

On the high-purity isopropyl alcohol obtained as described above, in the same manner as in Example 1, acceleration tests under temperature conditions of 80° C. and 120° C. were performed, and the evaluation of the acetal compound was performed. Consequently, the concentration of the acetal compound was 89 ppb (table 6) at 80° C. and was 100 ppb (table 7) at 120° C.

Comparative Example 2

In the same manner as in Example 2 except that reduced-pressure distillation in Example 2 (purification of crude isopropyl alcohol) was changed to atmospheric distillation under conditions in which the reflux ratio was 3, the temperature of the oil bath was 120° C., the temperature of the tower top was 82° C. and the temperature of the cooler was 25° C., a high-purity isopropyl alcohol in which the concentration of isopropyl alcohol excepting water was equal to or greater than 99.999, by mass was manufactured. For the obtained high-purity isopropyl alcohol, the concentrations of the acetal compound, the aldehyde compound and the ketone compound were measured, and the results thereof are shown in tables 3 to 5. For the obtained high-purity isopropyl alcohol, a water content was measured, and the result thereof is also shown in table 3.
(Acceleration Test)

On the high-purity isopropyl alcohol obtained as described above, in the same manner as in Example 1, acceleration tests under temperature conditions of 80° C. and 120° C. were performed, and the evaluation of the acetal compound was performed. Consequently, the concentration of the acetal compound was 270 ppb (table 6) at 80° C. and was 900 ppb (table 7) at 120° C.

Comparative Example 3

In the same manner as in Example 2 except that atmospheric distillation in Example 2 (purification of crude isopropyl alcohol) was changed to reduced-pressure distillation under conditions in which the pressure was 20 kPa, the number of plates was 10, the reflux ratio was 3, the temperature of the oil bath was 70° C., the temperature of the tower top was 35 to 45° C. and the temperature of the cooler was −5 to 0° C., a high-purity isopropyl alcohol in which the concentration of isopropyl alcohol excepting water was equal to or greater than 99.999, by mass was manufactured. For the obtained high-purity isopropyl alcohol, the concentrations of the acetal compound, the aldehyde compound and the ketone compound were measured, and the results thereof are shown in tables 3 to 5. For the obtained high-purity isopropyl alcohol, a water content was measured, and the result thereof is also shown in table 3.

(Acceleration Test)

On the high-purity isopropyl alcohol obtained as described above, in the same manner as in Example 1, acceleration tests under temperature conditions of 80° C. and 120° C. were performed, and the evaluation of the acetal compound was performed. Consequently, the concentration of the acetal compound was 200 ppb (table 6) at 80° C. and was 190 ppb (table 7) at 1?0° C.

TABLE 3

| | Concentrations in high-purity isopropyl alcohol C7-C12 acetal compound (ppb) | | | | Water content (ppm) |
|---|---|---|---|---|---|
| | C8 acetal | C9 acetal | Other acetals | Acetal compound total | |
| Example 2 | 2 | 3 | 1 or less | 6 or less | 10 |
| Example 3 | 2 | 3 | 1 or less | 6 or less | 10 |
| Example 4 | 2 | 3 | 1 or less | 6 or less | 10 |
| Example 5 | 2 | 3 | 1 or less | 6 or less | 5 |
| Example 6 | 70 | 20 | 1 | 91 | 10 |
| Comparative Example 2 | 5 | 10 | 1 or less | 16 or less | 5 |
| Comparative Example 3 | 100 | 100 | 10 | 210 | 10 |

TABLE 4

| | Concentrations in high-purity isopropyl alcohol C1-C6 aldehyde compound (ppb) | | | |
|---|---|---|---|---|
| | Acetaldehyde | Propionaldehyde | Butyraldehyde | Aldehyde compound total |
| Example 2 | 400 | 500 | 200 | 1100 |
| Example 3 | 100 | 80 | 100 | 280 |
| Example 4 | 50 | 40 | 30 | 120 |
| Example 5 | 30 | 20 | 10 | 60 |
| Example 6 | 50 | 40 | 30 | 120 |

TABLE 4-continued

| | Concentrations in high-purity isopropyl alcohol C1-C6 aldehyde compound (ppb) | | | |
|---|---|---|---|---|
| | Acetaldehyde | Propionaldehyde | Butyraldehyde | Aldehyde compound total |
| Comparative Example 2 | 800 | 1200 | 300 | 2300 |
| Comparative Example 3 | 50 | 40 | 30 | 120 |

TABLE 5

| | Concentrations in high-purity isopropyl alcohol C3-C6 ketone compound (ppb) | | | |
|---|---|---|---|---|
| | Acetone | 2-Pentanone | 3-Methyl-2-pentanone | Ketone compound total |
| Example 2 | 500 | 500 | 10 | 1010 |
| Example 3 | 500 | 200 | 1 | 701 |
| Example 4 | 100 | 50 | 1 | 151 |
| Example 5 | 100 | 50 | 1 | 151 |
| Example 6 | 100 | 50 | 100 | 250 |
| Comparative Example 2 | 500 | 1000 | 50 | 1550 |
| Comparative Example 3 | 100 | 50 | 5 | 155 |

TABLE 6

| | Concentration of C7-C12 acetal compound in high-purity isopropyl alcohol after acceleration test of 80° C. (ppb) | | | | Amount of increase in C7-C12 acetal compound by acceleration test |
|---|---|---|---|---|---|
| | C8 acetal | C9 acetal | Other acetals | Acetal compound total | |
| Example 2 | 25 | 40 | 25 | 90 | 18 times |
| Example 3 | 10 | 15 | 15 | 40 | 8 times |
| Example 4 | 6 | 10 | 3 | 19 | 4 times |
| Example 5 | 4 | 6 | 1 | 11 | 2 times |
| Example 6 | 55 | 30 | 4 | 89 | 1.2 times |
| Comparative Example 2 | 100 | 150 | 20 | 270 | 18 times |
| Comparative Example 3 | 95 | 95 | 10 | 200 | 1 time |

TABLE 7

| | Concentration of C7-C12 acetal compound in high-purity isopropyl alcohol after acceleration test of 120° C. (ppb) | | | | Amount of increase in C7-C12 acetal compound by acceleration test |
|---|---|---|---|---|---|
| | C8 acetal | C9 acetal | Other acetals | Acetal compound total | |
| Example 2 | 100 | 200 | 50 | 350 | 70 times |
| Example 3 | 30 | 30 | 25 | 85 | 17 times |
| Example 4 | 10 | 12 | 5 | 27 | 6 times |
| Example 5 | 6 | 8 | 1 | 15 | 3 times |
| Example 6 | 60 | 35 | 5 | 100 | 1.3 times |
| Comparative Example 2 | 300 | 500 | 100 | 900 | 60 times |
| Comparative Example 3 | 90 | 90 | 10 | 190 | 0.9 times |

TABLE 7-continued

| | Concentration of C7-C12 acetal compound in high-purity isopropyl alcohol after acceleration test of 120° C. (ppb) | | | | Amount of increase in C7-C12 acetal compound by acceleration test |
|---|---|---|---|---|---|
| | C8 acetal | C9 acetal | Other acetals | Acetal compound total | |
| Example 3 | | | | | |

The entire disclosure of Japanese Patent Application No. 2018-188017 filed on Oct. 3, 2018 is incorporated in the present specification by reference.

The invention claimed is:

1. A cleaning liquid formed of a high-purity isopropyl alcohol and used in a semiconductor manufacturing process,
    wherein a water content is 3 to 25 ppm by mass,
    a concentration of an aldehyde compound having 1 to 6 carbon atoms is 10 to 500 ppb by mass,
    a concentration of a ketone compound having 3 to 6 carbon atoms is 50 to 1000 ppb by mass,
    a concentration of an acetal compound having 7 to 12 carbon atoms is equal to or less than 100 ppb by mass, and
    when an acceleration test for performing heating at 120° C. for 4 hours is performed under a nitrogen atmosphere, an amount of increase in the concentration of the acetal compound is 30 or less times a value before the heating, and the concentration of the acetal compound is maintained to be a value equal to or less than 100 ppb by mass.

2. A method for manufacturing the high-purity isopropyl alcohol in which a concentration of an acetal compound having 7 to 12 carbon atoms is equal to or less than 100 ppb by mass, and in which when an acceleration test for performing heating at 120° C. for 4 hours is performed under a nitrogen atmosphere, an amount of increase in the concentration of the acetal compound is 30 or less times a value before the heating and the concentration of the acetal compound is maintained to be a value equal to or less than 100 ppb by mass, the method comprising:
    a reduced-pressure distillation step of distilling a low-boiling portion by reduced-pressure distillation so as to perform purification until a concentration of an aldehyde compound having 1 to 6 carbon atoms is reduced to be equal to or less than 500 ppb by mass and a concentration of a ketone compound having 3 to 6 carbon atoms is reduced to be equal to or less than 1000 ppb by mass; and
    an atmospheric distillation step of removing a bottom liquid by atmospheric distillation so as to perform purification until the concentration of the acetal compound having 7 to 12 carbon atoms is reduced to be equal to or less than 100 ppb by mass,
    wherein:
        the reduced-pressure distillation step and the atmospheric distillation step are combined to be performed on crude isopropyl alcohol,
        the pressure of the reduced-pressure distillation step is equal to or less than 10 kPa, and
        the crude isopropyl alcohol is obtained by a direct hydration method of propylene.

* * * * *